(12) United States Patent
Woodward

(10) Patent No.: US 8,238,997 B2
(45) Date of Patent: Aug. 7, 2012

(54) CHIN ADHESIVE AND METHOD FOR USE

(76) Inventor: Grady Woodward, Seattle, WA (US)

( * ) Notice: Subject to any disclaimer, the term of this patent is extended or adjusted under 35 U.S.C. 154(b) by 590 days.

(21) Appl. No.: 12/372,031

(22) Filed: Feb. 17, 2009

(65) Prior Publication Data

US 2010/0210935 A1 Aug. 19, 2010

(51) Int. Cl.
*A61B 5/0492* (2006.01)
(52) U.S. Cl. .................. 600/383; 600/391; 600/547
(58) Field of Classification Search .................. 600/383, 600/391, 392, 547; 607/139, 140
See application file for complete search history.

(56) References Cited

U.S. PATENT DOCUMENTS

| | | | | |
|---|---|---|---|---|
| 4,827,939 A | * | 5/1989 | Cartmell et al. | 600/392 |
| 4,890,608 A | * | 1/1990 | Steer | 602/57 |
| 7,113,815 B2 | * | 9/2006 | O'Neil et al. | 600/344 |
| 7,158,822 B2 | * | 1/2007 | Payne, Jr. | 600/390 |
| 8,121,696 B2 | * | 2/2012 | Vallero | 607/46 |
| 2005/0059869 A1 | * | 3/2005 | Scharf et al. | 600/340 |
| 2010/0056882 A1 | * | 3/2010 | Moore et al. | 600/301 |

* cited by examiner

*Primary Examiner* — Lee S Cohen
(74) *Attorney, Agent, or Firm* — Priya Sinha Cloutier

(57) ABSTRACT

The current invention is an apparatus that comfortably fits on an individual's chin and holds electrodes in place.

3 Claims, 3 Drawing Sheets

CHIN ADHESIVE AND METHOD FOR USE

CROSS-REFERENCES TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND

Electromyograph (EMG) is an instrument that is used to evaluate and record activation signals in muscle. The EMG detects the electrical potential generated when muscle cells are at rest or contract. There are two types of EMG: intramuscular and surface. Intramuscular EMS consists of placing a needle electrode into the muscle in question and consequently, may be too invasive. Surface EMG consist of placing an electrode on the surface of the skin. This allows the medical professional to obtain a general picture of muscle activation; intramuscular EMG allows the medical professional to monitor the activities of a few fibers.

Surface EMG is generally used to evaluate patients with neuromuscular diseases, low back pain, and disorders of motor control. It is also used in sleep clinics to determine the quality of sleep an individual is having. In this case, electrodes are placed on several regions of the face; one of those regions being the chin area.

However, as medical personal have found out, the electrodes that are required on the chin area are difficult to keep in place. Usually, medical professionals use medical adhesive to keep electrodes in place. However, this method often fails as it is easy for a sleeping person to remove or loosen a seeming irritant from his face. The current invention addresses this issue. The current invention is an apparatus that comfortably fits on an individual's chin and holds EMG electrodes in place.

BRIEF SUMMARY OF THE INVENTION

The current invention is an apparatus that comfortably fits on an individual's chin and holds electrodes in place.

BRIEF DESCRIPTION OF THE SEVERAL VIEWS OF THE DRAWINGS

Other features and advantages of the present invention will become apparent in the following detailed descriptions of the preferred embodiment with reference to the accompanying drawings, of which.

DETAILED DESCRIPTION OF THE INVENTION

Figure 1:
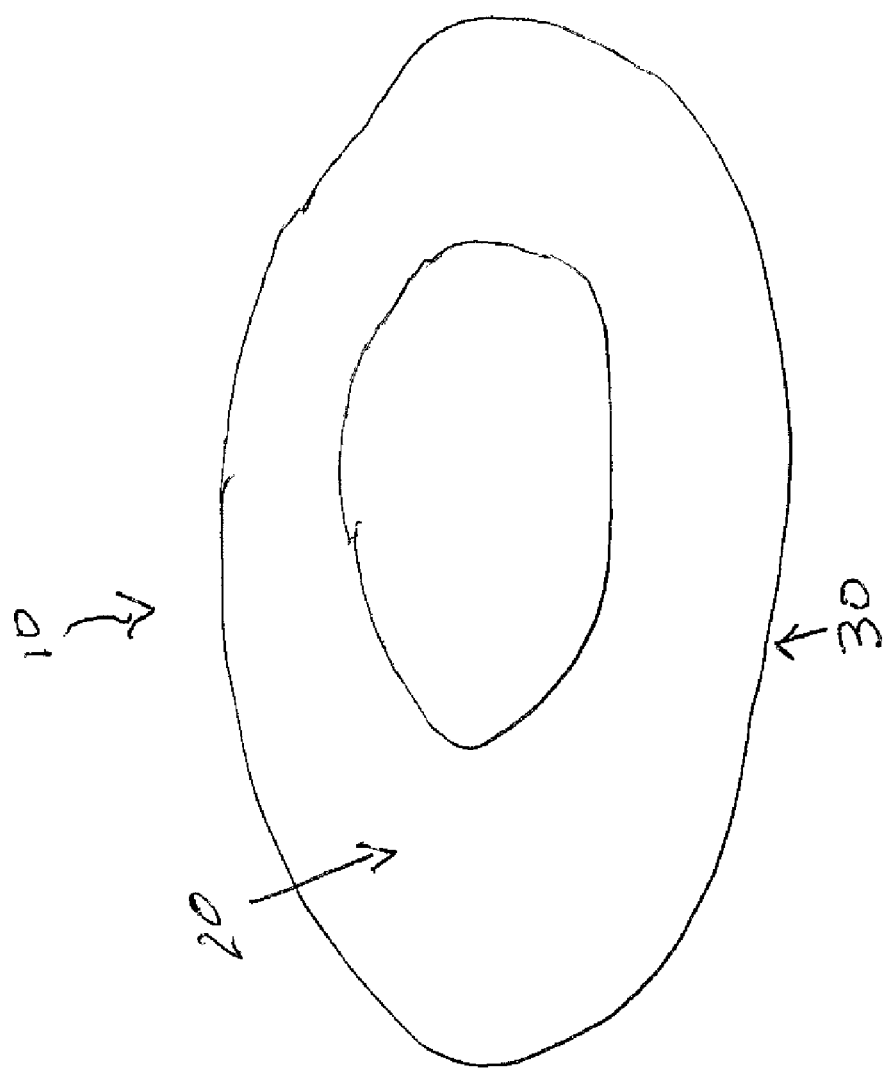
FIG. 1 is a top view of the chin adhesive.
Figure 2:
FIG. 2 is a front elevational view of the chin adhesive as used on an individual.
Figure 3:
FIG. 3 is a side elevational view of the chin adhesive as used on an individual.

The present invention is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete and will fully convey the scope of the invention to those skilled in the art.

The current apparatus (10) is used to hold surface EMG electrode in place around a chin. The apparatus (10) comprises a front side (20) and a back side (30). The back side (30) comprises adhesive material; said adhesive material is strong enough to hold an EMG electrode is place but can be easily removed. The apparatus (10) can be made of breathable or non-breathable material.

The apparatus (10) is shaped as a oval; the center of the oval defines a hole. The apparatus (10) is shaped as an oval because it fits naturally over the chin. Preferably, the apparatus is manufactured with varying radii allowing proper fit on differently sized individuals. Also, although the current apparatus has been described as being used with an EMG, a person with ordinary skill in the art will know that the apparatus can be with any electrode or medical equipment that needs to be attached to the chin area.

What is claimed:

1. A method of monitoring an electrical signal from an electrode near a human chin comprised of:
   a. placing an electrode near or on the chin using an apparatus comprised of a substrate shaped as an oval; where the oval has a front side and a back side; where the substrate defines a hole at the center of the oval; where the back side comprises an adhesive which removably attaches to human skin and an electrode;
   b. positioning the substrate so that the hole is located over a human chin with the back side facing the human skin;
   c. attaching the electrode to the back side of the substrate using the adhesive;
   d. monitoring the electrical signal detected by the electrode.

2. The method of claim 1 where the adhesive is of sufficient strength to hold an electrode in place.

3. The method of claim 1 where the adhesive is easily removed from the human skin.

* * * * *